United States Patent
Molloy et al.

(10) Patent No.: US 11,759,400 B2
(45) Date of Patent: Sep. 19, 2023

(54) PERSONAL PRESCRIPTION DISPENSER

(71) Applicant: International Business Machines Corporation, Armonk, NY (US)

(72) Inventors: Christopher L. Molloy, Raleigh, NC (US); Robert S. Milligan, Erlanger, KY (US); Steven A. Waite, Racine, WI (US); Gordan G. Greenlee, Endicott, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 17/465,431

(22) Filed: Sep. 2, 2021

(65) Prior Publication Data

US 2021/0393487 A1 Dec. 23, 2021

Related U.S. Application Data

(62) Division of application No. 16/215,311, filed on Dec. 10, 2018, now Pat. No. 11,154,460.

(51) Int. Cl.
*A61J 7/04* (2006.01)
*A61J 7/02* (2006.01)
(Continued)

(52) U.S. Cl.
CPC . *A61J 7/04* (2013.01); *A61J 7/02* (2013.01); *G16H 20/13* (2018.01); *H04L 67/12* (2013.01)

(58) Field of Classification Search
CPC .. G16H 20/10; G16H 20/13; A61J 7/04; A61J 7/02; H04L 67/12
(Continued)

(56) References Cited

U.S. PATENT DOCUMENTS

| 2,027,670 | A |   | 1/1936 | Broeren |
| 2,758,710 | A | * | 8/1956 | Egmont ............. B65D 83/0847 206/532 |

(Continued)

FOREIGN PATENT DOCUMENTS

| EP | 2463211 A1 | 6/2012 |
| KR | 20170127587 A * | 11/2017 ............. G16H 10/00 |

(Continued)

OTHER PUBLICATIONS

"List of IBM Patents or Patent Applications Treated As Related," for U.S. Appl. No. 17/465,431, filed Sep. 2, 2021.

*Primary Examiner* — Rakesh Kumar
(74) *Attorney, Agent, or Firm* — Patterson + Sheridan, LLP

(57) ABSTRACT

Disclosed is a method and apparatus for transporting and dispensing medications for a patient according to a medication schedule for the patient. A smart container from a pharmacy is received at the patient's site and the container is checked to make sure that the container was delivered to the correct patient site. The smart container contains a memory device that contains identification information of the patient, dosage and treatment instructions for the patient. This information and the medication were checked for compatibility before the smart container was delivered. The identity of the patient at the patient's site is then checked and the patient performs on or more biometric tests before the medication is dispensed by the smart container. Upon taking the medication and providing video proof thereof, the smart container is returned to the pharmacy.

17 Claims, 21 Drawing Sheets

(51) Int. Cl.
*G16H 20/13* (2018.01)
*H04L 67/12* (2022.01)

(58) Field of Classification Search
USPC ...... 364/479, 413.02, 413.03, 413.04, 513.5;
700/242, 237, 236, 240; 221/2, 9, 15,
221/197, 13, 82, 7, 71, 92, 191, 131
See application file for complete search history.

(56) References Cited

U.S. PATENT DOCUMENTS

| | | | |
|---|---|---|---|
| 3,325,052 A | 6/1967 | Sauber | |
| 3,398,857 A | 8/1968 | Alio | |
| 3,526,317 A * | 9/1970 | Vanders | B65D 75/30 206/217 |
| 4,223,801 A * | 9/1980 | Carlson | A61J 7/0472 206/533 |
| 4,530,447 A | 7/1985 | Greenspan | |
| 4,695,954 A * | 9/1987 | Rose | G07F 17/0092 221/9 |
| 4,725,997 A * | 2/1988 | Urquhart | A61J 7/0436 368/10 |
| 4,732,411 A * | 3/1988 | Siegel | G09F 3/10 283/70 |
| 4,767,022 A * | 8/1988 | Oldorf | G07F 11/18 221/92 |
| 4,798,309 A * | 1/1989 | Stone | A61J 7/0481 221/15 |
| 4,811,871 A | 3/1989 | Wass et al. | |
| 4,911,327 A * | 3/1990 | Shepherd | A61J 7/0481 221/3 |
| 4,975,295 A * | 12/1990 | Sierra | A23F 5/385 426/594 |
| 5,057,305 A * | 10/1991 | Aberg | A61K 8/02 424/44 |
| 5,228,860 A * | 7/1993 | Hale | G09B 19/22 434/129 |
| 5,291,191 A * | 3/1994 | Moore | A61J 7/0445 340/5.91 |
| 5,329,459 A * | 7/1994 | Kaufman | A61B 5/4833 221/9 |
| 5,392,952 A * | 2/1995 | Bowden | A61J 7/0481 221/76 |
| 5,587,277 A * | 12/1996 | Yamashita | G03C 5/265 430/458 |
| 5,597,995 A | 1/1997 | Williams et al. | |
| 5,646,912 A * | 7/1997 | Cousin | G06V 20/66 221/96 |
| 5,907,493 A | 5/1999 | Boyer et al. | |
| 5,945,651 A * | 8/1999 | Chorosinski | A61J 1/035 235/375 |
| 6,202,923 B1 | 3/2001 | Boyer et al. | |
| 6,259,654 B1 * | 7/2001 | de la Huerga | A61J 7/0481 368/10 |
| 6,332,100 B1 * | 12/2001 | Sahai | G16H 20/13 700/242 |
| 6,439,422 B1 * | 8/2002 | Papp | A61J 7/0084 221/13 |
| 6,751,730 B1 | 6/2004 | Walker et al. | |
| 7,213,721 B2 | 5/2007 | Abdulhay et al. | |
| 7,263,411 B2 | 8/2007 | Shows et al. | |
| 7,289,879 B2 | 10/2007 | William et al. | |
| 7,344,047 B2 * | 3/2008 | Gilmore | G07F 17/0092 221/13 |
| 7,533,776 B2 | 5/2009 | Nickerson | |
| 7,559,436 B2 | 7/2009 | Bieger | |
| 7,711,449 B2 | 5/2010 | Abdulhay et al. | |
| 7,747,477 B1 * | 6/2010 | Louie | G07G 1/009 705/28 |
| 7,831,334 B2 | 11/2010 | Vollm et al. | |
| 7,896,192 B2 * | 3/2011 | Conley | G07F 17/0092 221/92 |
| 7,978,564 B2 | 7/2011 | De La Huerga | |
| 8,019,471 B2 | 9/2011 | Bogash et al. | |
| 8,112,175 B2 * | 2/2012 | Handfield | A61J 7/0084 700/242 |
| 8,175,891 B2 | 5/2012 | Berkelhamer et al. | |
| 8,326,455 B2 * | 12/2012 | Dunn | G07F 9/02 221/211 |
| 8,364,504 B1 * | 1/2013 | Bleser | G16H 20/10 705/2 |
| 9,150,119 B2 | 10/2015 | Henderson et al. | |
| 9,177,265 B2 * | 11/2015 | Bartfeld | G06V 20/66 |
| 9,505,530 B2 | 11/2016 | Downey et al. | |
| 9,697,335 B2 | 7/2017 | Joplin | |
| 9,975,688 B2 * | 5/2018 | Benouali | B65D 51/26 |
| 10,204,704 B1 * | 2/2019 | Wurst | G16H 10/20 |
| 10,235,499 B1 | 3/2019 | Bleser et al. | |
| 10,311,536 B1 | 6/2019 | Ansari et al. | |
| 10,555,873 B2 * | 2/2020 | Poirier | A61J 7/0076 |
| 11,154,460 B2 * | 10/2021 | Molloy | A61J 7/0436 |
| 11,568,973 B1 * | 1/2023 | Akinwale | G16H 20/10 |
| 2002/0055856 A1 * | 5/2002 | Adams | G06Q 10/08 705/2 |
| 2003/0127463 A1 * | 7/2003 | Varis | G07F 11/62 221/13 |
| 2003/0221687 A1 | 12/2003 | Kaigler | |
| 2004/0074917 A1 * | 4/2004 | McHutchinson | B65D 83/0463 221/302 |
| 2005/0022451 A1 | 2/2005 | Fitzgibbon et al. | |
| 2007/0093935 A1 | 4/2007 | Fu | |
| 2009/0006126 A1 * | 1/2009 | Champigny | G16H 20/10 705/2 |
| 2009/0024416 A1 * | 1/2009 | McLaughlin | G16H 10/65 705/2 |
| 2009/0105876 A1 * | 4/2009 | Simpson | G07F 9/026 700/242 |
| 2009/0138122 A1 | 5/2009 | Wagner | |
| 2009/0167531 A1 * | 7/2009 | Ferguson | G16H 40/67 340/572.1 |
| 2009/0281657 A1 * | 11/2009 | Gak | G07F 17/0092 700/242 |
| 2010/0076595 A1 | 3/2010 | Nguyen | |
| 2011/0202174 A1 * | 8/2011 | Bogash | G07F 9/026 700/242 |
| 2013/0096938 A1 | 4/2013 | Stueckemann et al. | |
| 2013/0222116 A1 * | 8/2013 | Barry, III | G16H 40/20 340/10.1 |
| 2014/0180705 A1 | 6/2014 | Stueckemann et al. | |
| 2014/0278510 A1 * | 9/2014 | McLean | G16H 20/13 705/2 |
| 2014/0379381 A1 * | 12/2014 | Turkanis | G16Z 99/00 705/3 |
| 2015/0242592 A1 | 8/2015 | Weiss et al. | |
| 2015/0317454 A1 | 11/2015 | Kruger | |
| 2015/0359711 A1 * | 12/2015 | Ducatt | G16Z 99/00 221/13 |
| 2016/0246943 A1 | 8/2016 | Lake et al. | |
| 2016/0283691 A1 * | 9/2016 | Ali | G16H 20/13 |
| 2016/0300031 A1 * | 10/2016 | Salwan | G06F 16/9535 |
| 2016/0321406 A1 * | 11/2016 | Timmerman | G16H 20/10 |
| 2016/0342744 A1 | 11/2016 | Joao | |
| 2017/0197775 A1 | 7/2017 | Fagen et al. | |
| 2018/0040539 A1 | 2/2018 | Wang et al. | |
| 2018/0139043 A1 | 5/2018 | Jayachandran et al. | |
| 2018/0240539 A1 | 8/2018 | Doherty | |
| 2018/0285533 A1 | 10/2018 | Farhat | |
| 2018/0286506 A1 * | 10/2018 | Farhat | G06Q 20/085 |
| 2019/0035499 A1 * | 1/2019 | Daya | G16H 20/10 |
| 2019/0057763 A1 * | 2/2019 | Stockert | G16H 10/00 |
| 2019/0237176 A1 * | 8/2019 | O'brien | B64C 39/024 |
| 2019/0267123 A1 * | 8/2019 | Stueckemann | G06Q 30/06 |
| 2019/0300269 A1 | 10/2019 | Park | |
| 2020/0024063 A1 | 1/2020 | Gadd et al. | |
| 2022/0084665 A1 * | 3/2022 | Blackburn | G16H 40/67 |

FOREIGN PATENT DOCUMENTS

| | | | | |
|---|---|---|---|---|
| WO | WO-2008089249 A1 * | 7/2008 | | G06F 19/3456 |
| WO | WO-2017027974 A1 * | 2/2017 | | G06Q 50/22 |

(56) References Cited

FOREIGN PATENT DOCUMENTS

* cited by examiner

| neutralization, disposal bins | |
|---|---|
| 296a | 296b |
| 296c | 296d |
| 296e | 296f |
| 296g | 296h |
| 296i | 296j | medication bins 290

| | |
|---|---|
| 292r Flash RAM | 292a |
| 292b | 292c |
| 292d | 292e |
| 292f | 292g |
| 292h | 292i |
| 292j | 292k |

FIG. 2D

PERSONAL PRESCRIPTION DISPENSER

This application is a divisional of co-pending U.S. patent application Ser. No. 16/215,311, filed Dec. 10, 2018. The aforementioned related patent application is herein incorporated by reference in its entirety.

BACKGROUND

The present invention relates to dispensing medication at a patient's site, and more specifically, to use of secure systems and method to securely receive prescriptions from a medical provider, accurately fill the medications at a pharmacy and securely deliver the medications to the patient's site.

Patients at a residential site are often prescribed multiple medications to be taken under various different conditions and at different times. This process is beset with possible errors. For example, medication prescribed for a particular patient might be delivered to a different patient or might not be delivered at all; the medication might be tampered with prior to delivery to the patient; conditions for taking the medication properly might not be satisfied; possibly harmful interactions with other medications might escape attention; the patient might not actually take the medication; and the patient might take the medication at the proper times.

Thus, there is a need for an improved process for delivering and monitoring medications of a patient.

SUMMARY

According to one embodiment of the present invention, a method includes receiving, from a medical provider, a prescription associated with an identifier of a patient, in response to receiving the prescription, requesting and obtaining from the medical provider patient data including medical history of the patient, determining that the prescription is compatible with the patient data, adding medication according to the prescription to a secure container, and programming the secure container with the patient identifier and dosage information, including a dosage schedule according to the received prescription.

Further embodiments include a system configured to carry out one or more aspects of the above method and a computer readable medium containing instructions for carrying out one or more aspects of the above method.

BRIEF DESCRIPTION OF THE SEVERAL VIEWS OF THE DRAWINGS

FIG. 2D depicts medication bins and disposal bins in a smart container, according to one embodiment described herein.

DETAILED DESCRIPTION

Figure 1:
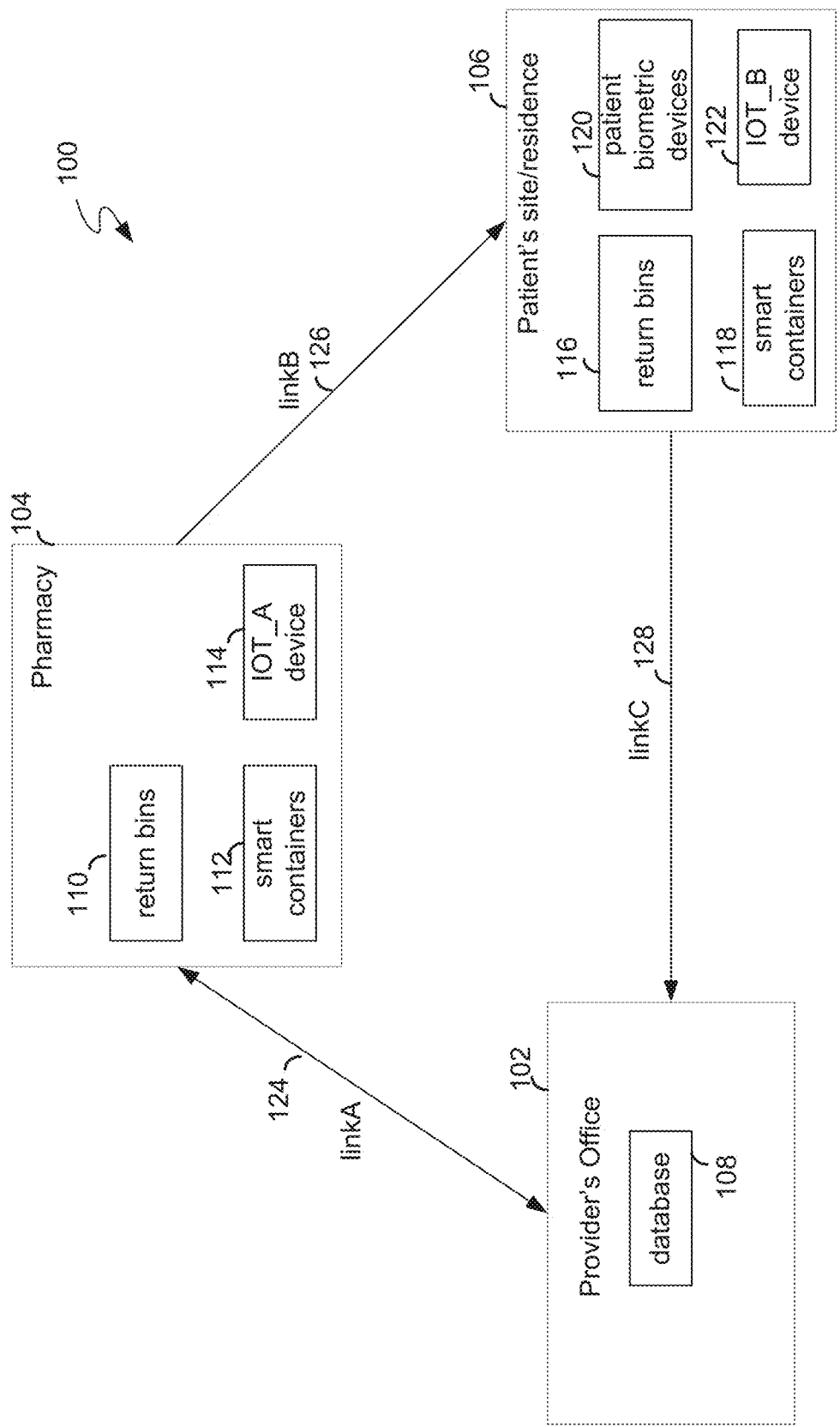
FIG. 1 depicts a system for providing medication to a patient, according to one embodiment described herein.

FIG. 1 depicts a system for providing medication to a patient. The system 100 includes a provider's office 102 with a database 108 for storing patient prescriptions, a pharmacy 104 with an IOT device 114, a number of smart and secure containers 112 for holding and transporting patient medication, an IOT (Internet of Things) device 114, a number of return bins 110 used for returning medication to the pharmacy 104, and a patient's site 106 with an IOT device 122, a number of return bins 116, smart and secure containers 118, and a number of patient biometric devices 122. The provider's office 102 communicates with the pharmacy 104 over link A 124. The pharmacy 104 communicates with the patient's site 106 over link B 126 and the patient's site 106 communicates with the provider's office 102 over link C 128. In some embodiments, communication links A 124, B 126 and C 128 are links through the Internet and messages sent and received over the Internet links are encrypted with public or private keys.

Messages sent and received over the various links, A 124, B 126 and C 128 occur without the sender or recipient being involved with the underlying communications media or its protocols. The messages can include any kind of data, programs, and/or objects. In particular, a step 'Send(msg to dest)' performed by a sender is an asynchronous non-blocking transmission of a message, msg, to a destination, dest, and a step, 'Received(msg)', is a predicate, which if true, is interpreted as signaling that the message, msg, has been received and is available to the recipient. If the predicate is false, no message has been received, and the recipient may be blocked waiting for a message to arrive. However, a recipient can configure the predicate so that by testing the predicate, the recipient can avoid being blocked.

Figure 2A:
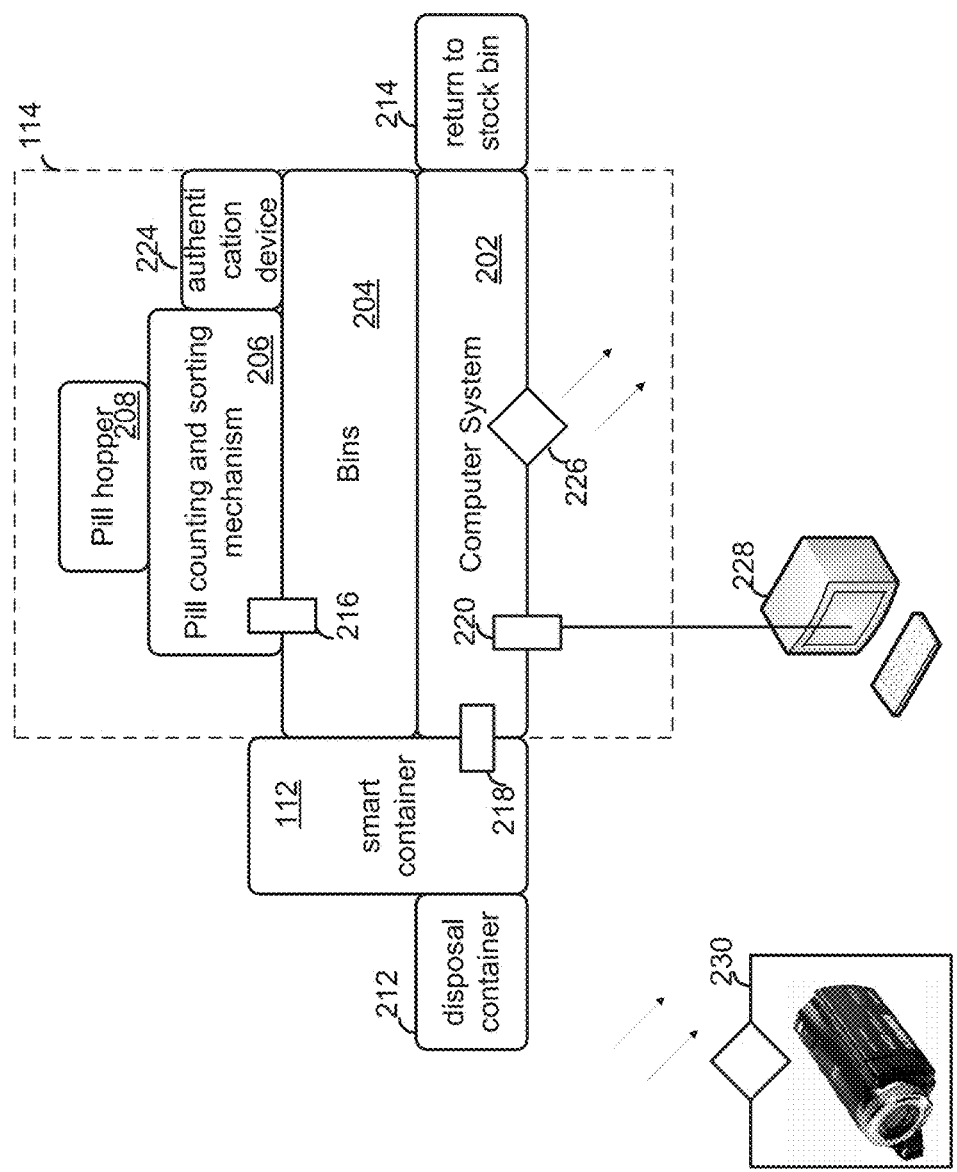
FIG. 2A depicts an IOT device at a pharmacy, according to one embodiment described herein.

FIG. 2A depicts an IOT device at a pharmacy, in an embodiment. The IOT device 114 includes a computer system 202, a number of medication bins 204, a pill counting and sorting mechanism 206, a pill hopper 208 and an authentication device 224, such as a fingerprint reader, video camera 230 or microphone 270. The pill counting and sorting mechanism 206 is connected to the bins via a USB port 216. One or more detachable smart and secure containers 112 are connected to the computer system 202 via a USB port 218. A monitor and keyboard 228 are attached to the computer system 202 via a USB port 220 and the video camera 230 is attached to the computer system 202 via a Bluetooth link 226 to the computer system 202.

Figure 2B:
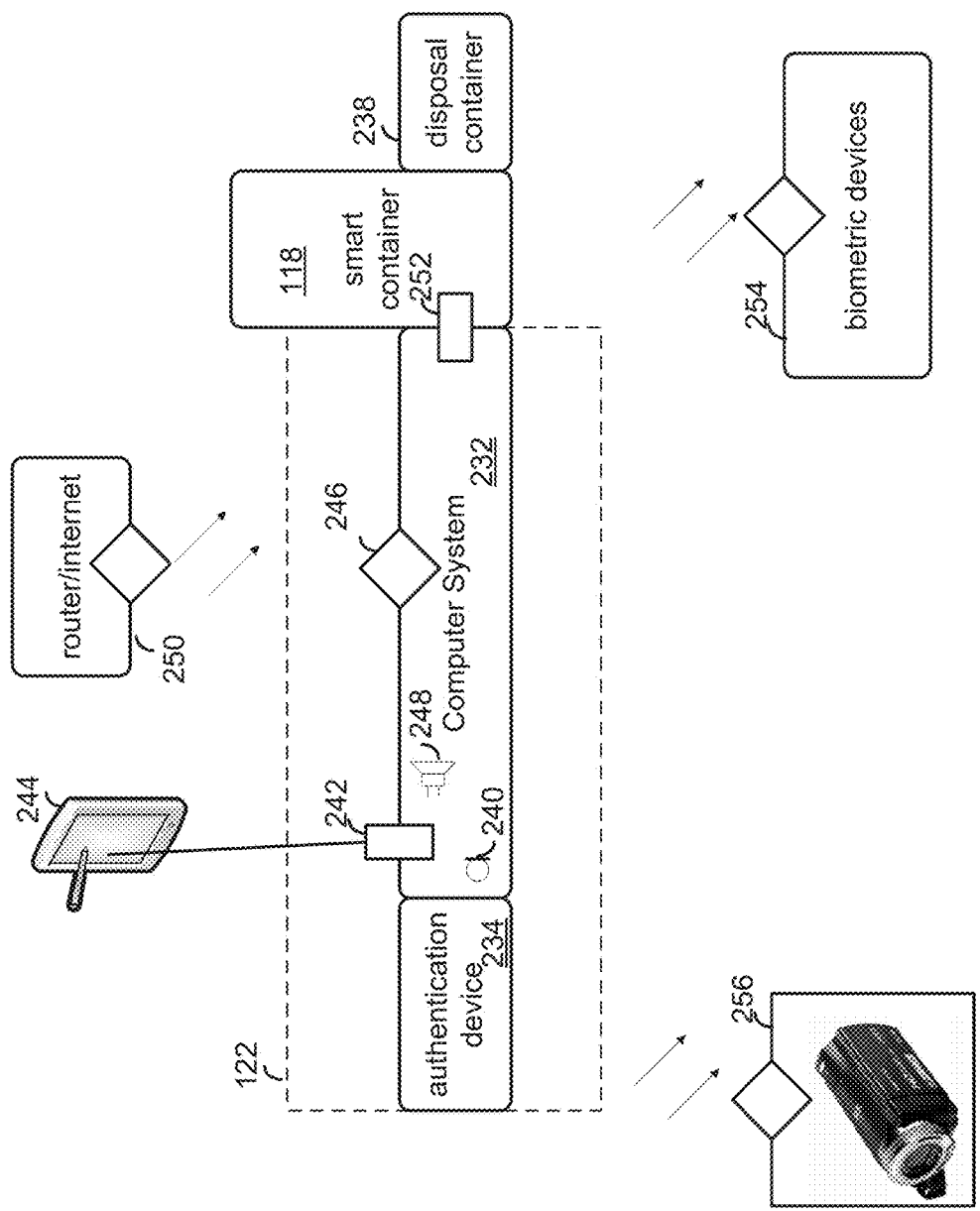
FIG. 2B depicts an IOT device at a patient location, according to one embodiment described herein.

FIG. 2B depicts an IOT device at a patient location, in an embodiment. The IOT device 122 includes a computer system 232 and an authentication device 234, such as a fingerprint reader. A detachable and tamper-proof (i.e., secure) smart container 118 and a display/touchpad device are respectively connected to the computer system 232 via USB ports 252 and 242. An Internet router 250, biometric devices 254 and a video camera 256 are connected to the computer system via Bluetooth link 246. The computer system includes a microphone 240 and speaker 248 for communicating with the patient.

Figure 2C:
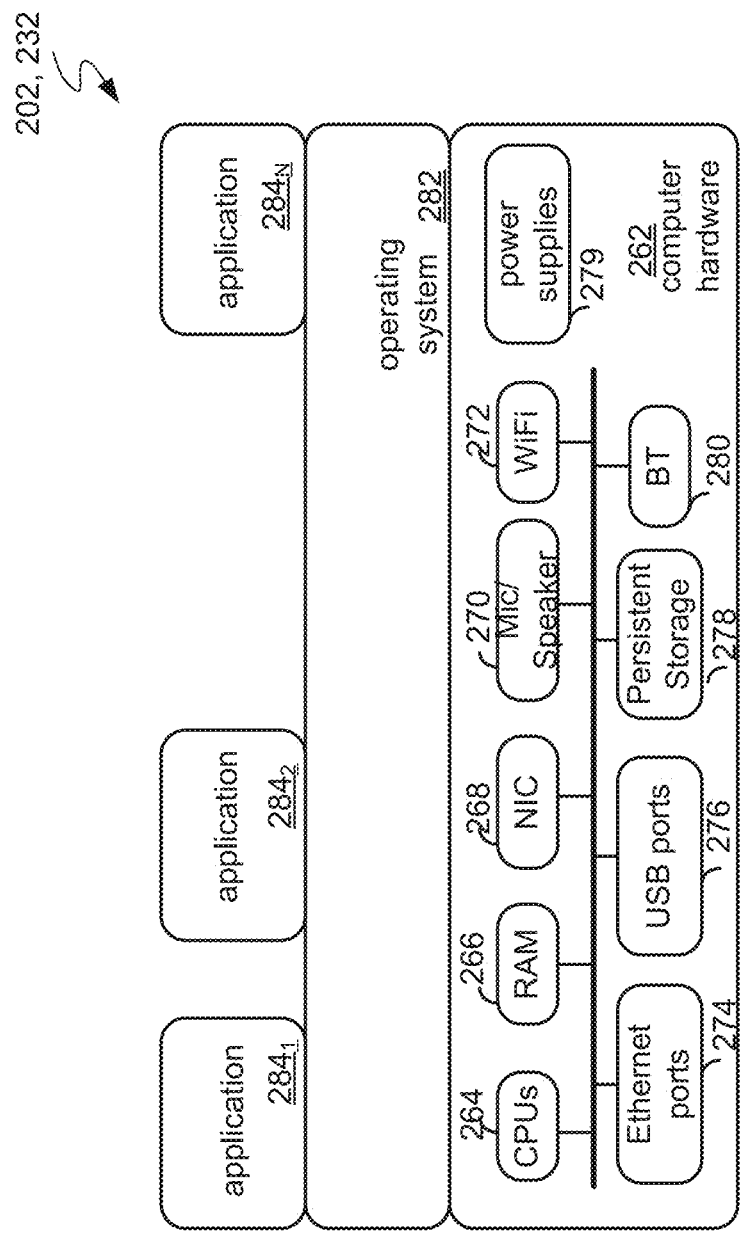
FIG. 2C depicts a computer system used in the IOT devices, according to one embodiment described herein.

FIG. 2C depicts a representative computer system used in the IOT devices, in an embodiment. The computer system 202, 232 includes computer hardware 262, an operating system 282 and one or more application programs $284_{1-N}$. The computer hardware includes one or more CPUs 265, RAM 266, NIC (Network interface component) 268, microphone and speaker interface 270, a WiFi port 272, Ethernet ports 274, USB ports 276, a Bluetooth link 280, persistent storage 278, and one or more power supplies 279 to power the computer hardware 262. In one embodiment, persistent storage 278 can be a form of RAID storage, such as RAID1. In one embodiment, the power supplies 279 can be redundant power supplies. The operating system 282 may a common commercial operating system such as the Windows® operating system or the Linux® operating system. The one or more application programs $284_{1-N}$ include programs and tasks for running the IOT devices 114, 122.

FIG. 2D depicts medication bins and disposal bins in a smart container, in an embodiment. The medication bins 290 include a plurality of tamper-proof (i.e., secure) storage bins 292a-k for medication along with a Flash RAM 292r that contains a public key/private key combination for authorization of the smart and secure container 112, 118 a patient token for a block chain record and treatment instructions for the medications contained in the storage bins 290. Each bin 292a-k is designed to be separately disengaged from the plurality of bins at the pharmacy 104 for re-use. A number of neutralization disposal bins 296a-j contain a neutralization agent for rendering medication inert. In one embodiment, the medication is rendered inert by an epoxy resin combination that is mixed with discarded medication.

Figure 2E:
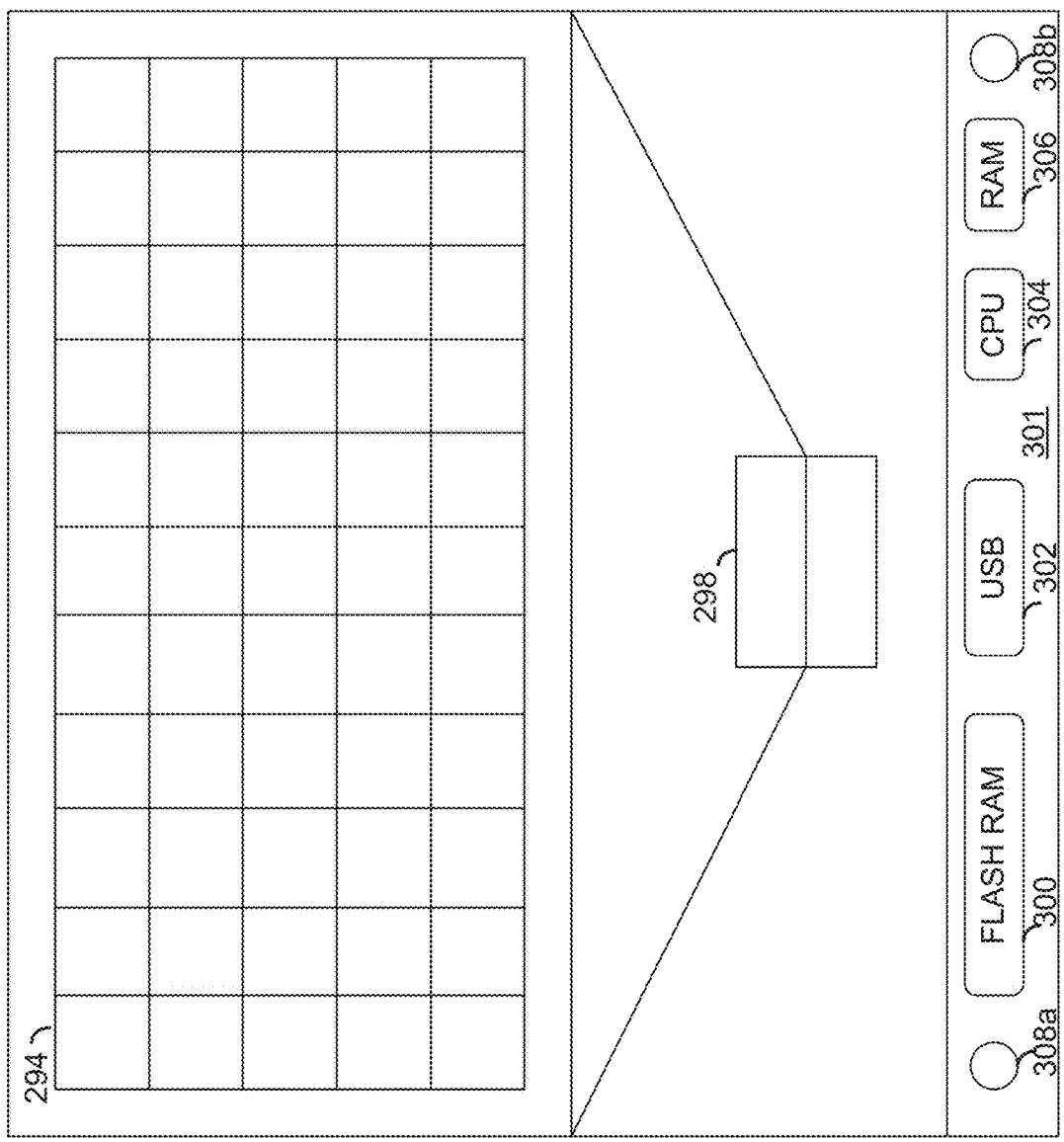
FIG. 2E depicts a portion of the smart container in more detail, according to one embodiment described herein.

FIG. 2E depicts a portion of the smart container in more detail, in an embodiment. Each one of the smart and secure containers 112, 118 includes a plurality of tamper-proof (i.e., secure) medication bins 294, a medication delivery bin 298, docking holes 308a, 308b for connecting to an IOT device, and computing hardware 301 and software. The computing hardware includes a CPU 304, RAM 306, which stores the software for execution by the CPU 304, the Flash RAM 292r, and one or more USB ports 302. The computing hardware 310 and software performs such tasks as authorization, block chain token updates, validation and processing treatment instructions, as described with respect to FIGS. 3 through 15.

Figure 2F:
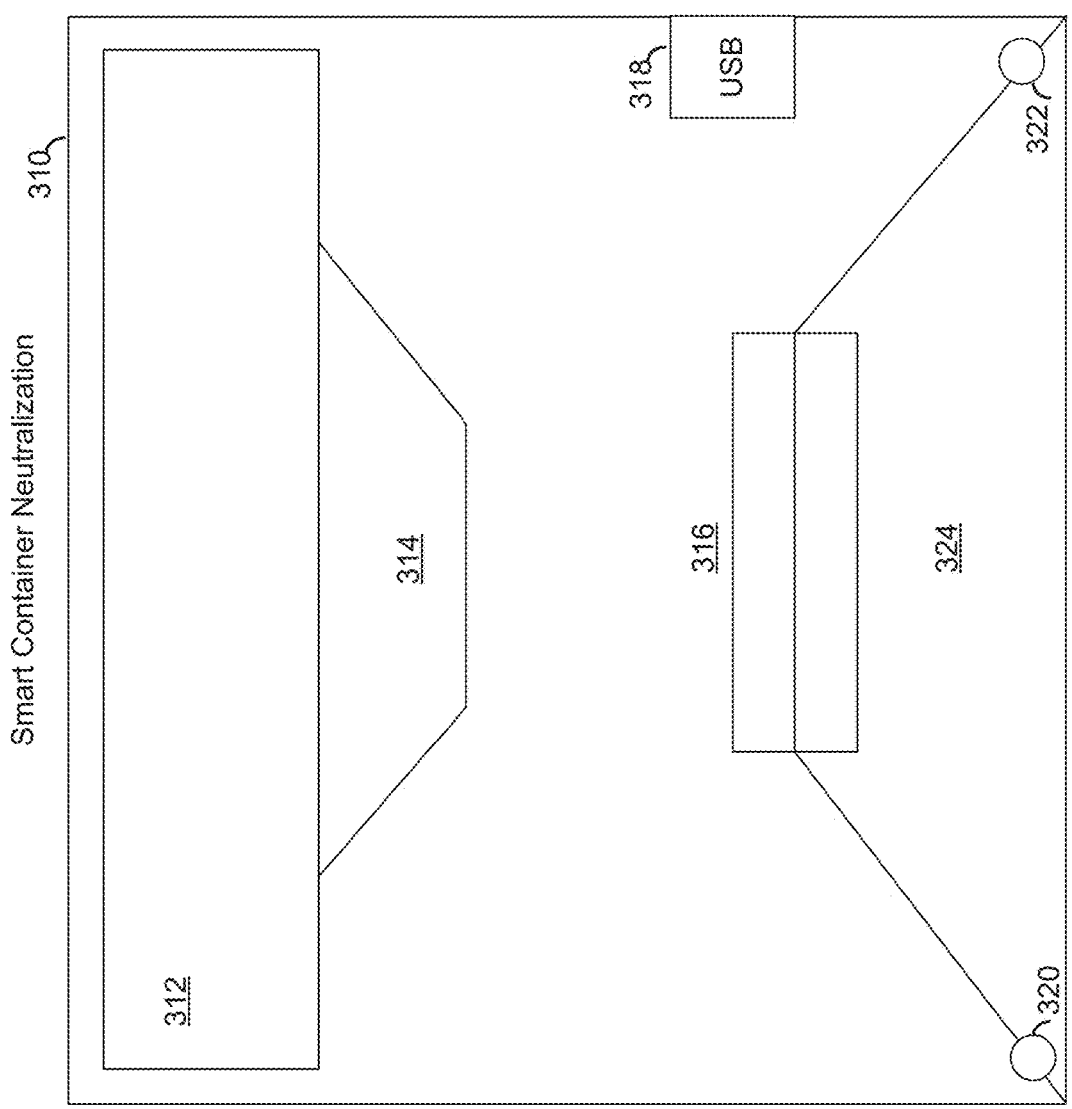
FIG. 2F depicts a portion of the smart container in more detail, according to one embodiment described herein.

FIG. 2F depicts a portion of the smart container in more detail, in an embodiment. FIG. 2F depicts the neutralization container 310 portion of the smart and secure container 112, 118. This portion of the smart and secure container 112, 118 includes a neutralization agent 312, a magnetic door 314, 316 for releasing the neutralization agent 312, a disposal bin 324 for holding the inert, discarded medication, a USB port 318 and docking holes 320, 322 for connecting to an IOT device.

Figure 3:
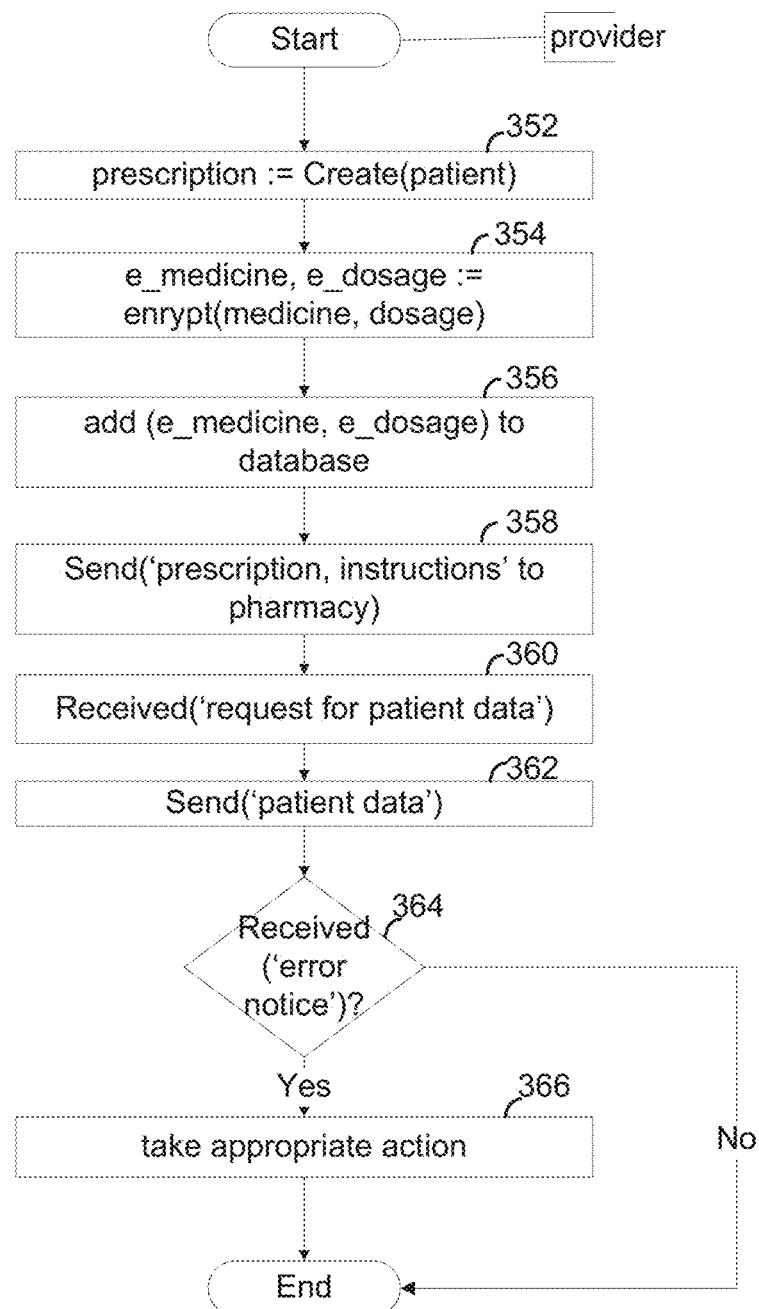
FIG. 3 depicts a flow chart of operations performed by a provider, according to one embodiment described herein.

FIG. 3 depicts a flow chart of operations performed by a medical provider, such as a doctor's office, in an embodiment. In step 352, the provider's office 102 creates a prescription for a patient. In step 354, the provider's office 102 encrypts the medication and dosages and in step 356, adds the encrypted items to the provider database 108. In step 358, the provider's office 102 sends the prescription along with instructions to the pharmacy 104. In one embodiment, transmission of the prescription is encrypted with a public key of the recipient and decrypted by the recipient using the recipient's corresponding private key.

In one embodiment, the prescription includes a superscription, an inscription, a subscription, a signature, refill information and a physician signature. The superscription includes the date, patient name, patient address. The inscription includes the name of the prescribed drug, the dosage form and strength of the drug. The subscription includes directions for the pharmacist, the size of each dose amount to be dispensed and the form of the drug (color, size, shape).

Continuing with FIG. 3, in step 360 the provider receives a 'request for patient data' message and in step 362 provides the patient data to the requestor. In one embodiment, the patient data includes the name of the patient, the medical history of the patient, the prescription history of the patient, notes and instructions. In step 364, the provider's office 102 determines whether notice of an error is received and if so, in step 366 takes appropriate actions depending on the type of error.

Figure 4:
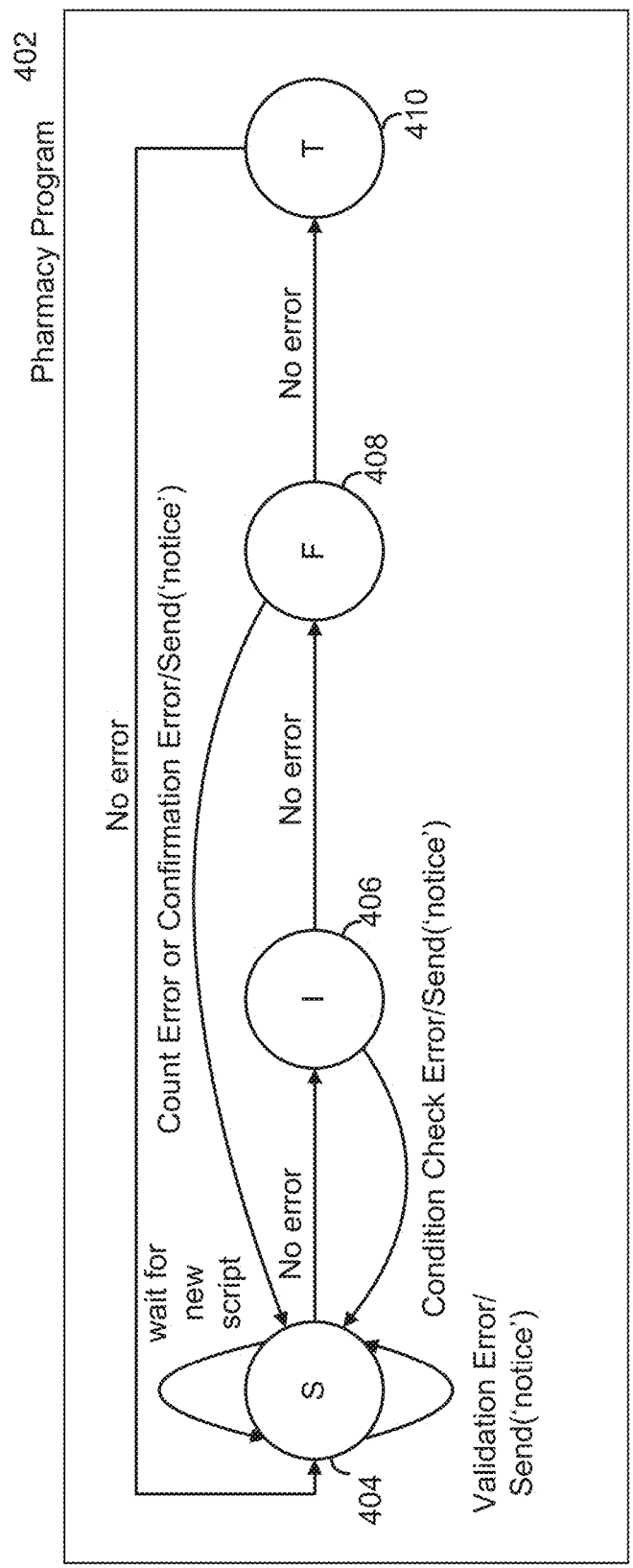
FIG. 4 depicts a flow chart of operations performed by a pharmacy IOT device, according to one embodiment described herein.

FIG. 4 depicts a pharmacy program running on a pharmacy IOT device, in an embodiment. In the embodiment depicted, the program 402 has four states S 404, I 406, F 408, and T 410. In state S 404, the Script function runs; in state I 406, the Interaction function; in state F 408, the Fill function; and in state T 410, the Transit function. Each of these functions is described in more detail below. In state S 404, the Script function waits for a new script and if the Script function runs without error, then the program 402 runs the Interaction function next. If the Interaction function runs without error, then the program 402 runs the Fill function next. If Interaction function encounters a condition check error, then a 'notice' message is sent to the last person involved in the process, which in this case is the provider's office 102, and the program 402 then runs the Script function. If the Fill function runs without error, then the program 402 runs the Transit function next. If the Fill function encounters a count error or confirmation error, then a 'notice' message is sent to the last person involved in the process, which is the pharmacy technician, and the program 402 runs the Script function. Thus, if no errors are encountered, the program 402 runs the Script, Interaction, Fill and Transit functions sequentially. Besides the error conditions mentioned above, other error conditions can be accommodated by the existing functions or added functions.

Figure 5:
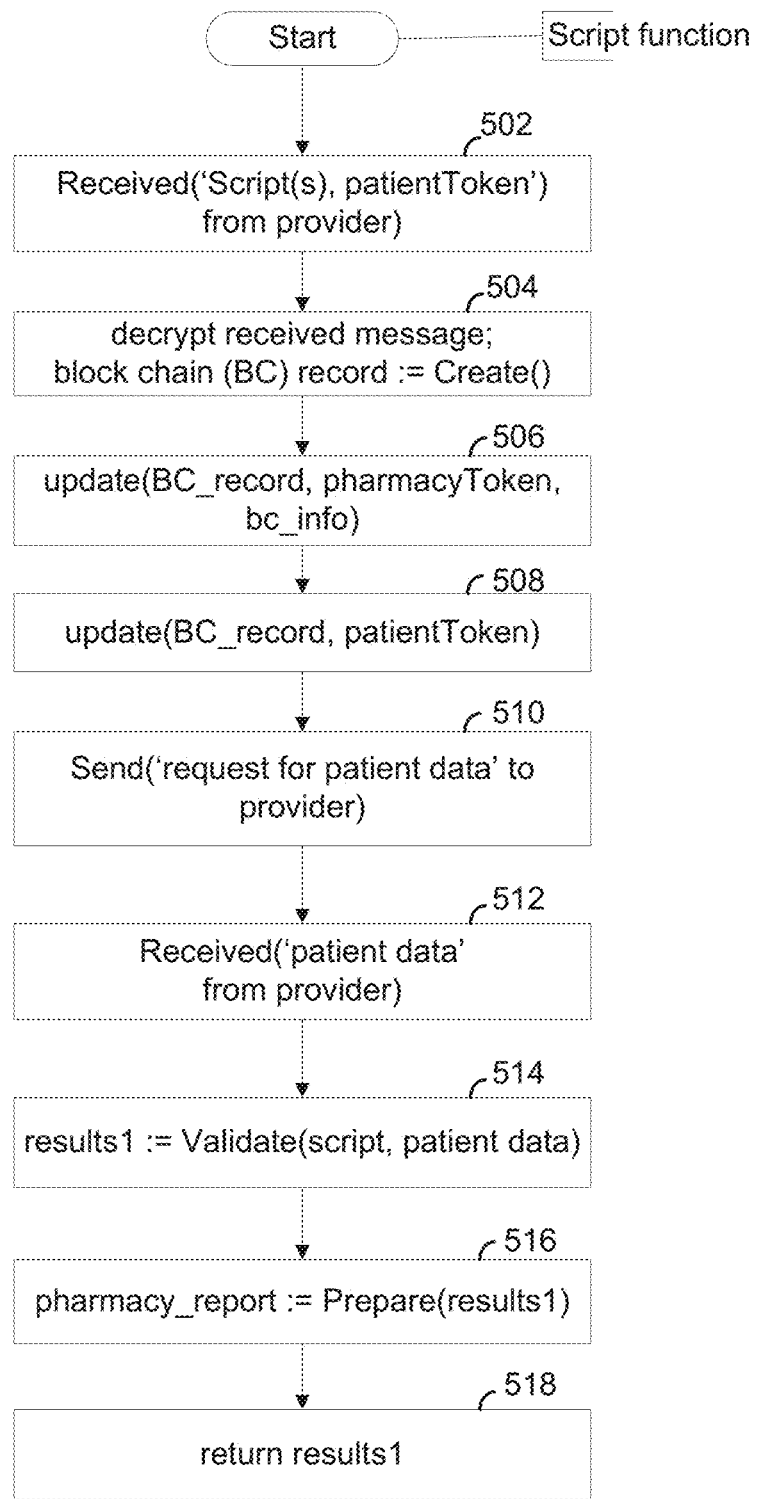
FIG. 5 depicts a flow chart of operations performed the Script function, according to one embodiment described herein.

FIG. 5 depicts a flow chart of operations performed the Script function, in an embodiment. In step 502, the Script function has received a 'Script(s), patientToken' message from the provider's office 102. The message contains one or more encrypted prescriptions for a patient identified by the patient token. In step 504, the Script function decrypts the data to create the plain text prescription and creates a block chain (BC) record. The block chain is used to track in a distributed ledger the transactions that occur throughout the system 100. In step 506, the Script function updates the newly created block chain record with the master block chain ID for the pharmacy and information such as the dosage details and a manufacturer of origin for each medication in the prescription. In step 508, the Script function updates the block chain record with the received token for the patient. In step 510, the Script function sends a 'request for patient data' message to the provider over link A 124 and in step 512, has received over link A 124 a message 'patient data', which contains the requested patient data from the provider's office 102. In an embodiment, the patient data is encrypted using a private key of the provider's office and is decrypted using the public key of the provider's office upon receipt at the pharmacy. In an embodiment, the patient data is sent by the provider to the pharmacy as part of the block chain record. In step 514, the Script function validates the prescription against the patient data. This guards against prescriptions that, based on the patient data, the patient may not be able to tolerate. In step 516, the Script function prepares a pharmacy report based on the results of step 514. In step 518, the Script function returns with a return value equal to the results, results1, of step 514. If the results indicate an error in the validation, then the IOT device program sends a 'notice' message to the last person involved in the process, i.e., a person in the provider's office, and waits for a new prescription.

Figure 6:
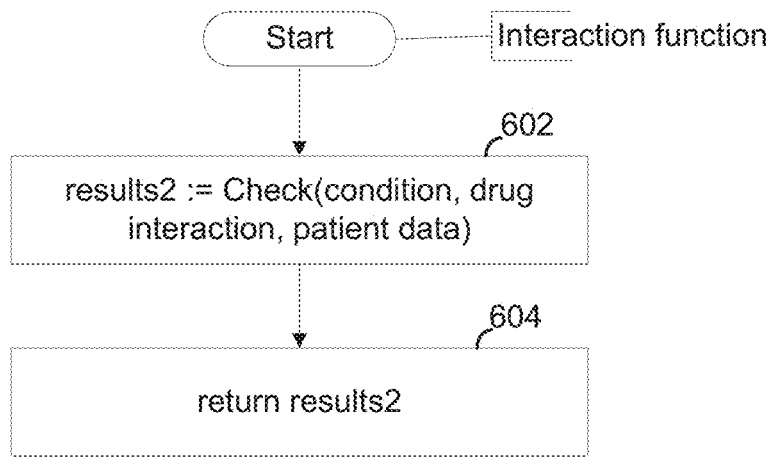
FIG. 6 depicts a flow chart of operations performed by the Interaction function, according to one embodiment described herein.

FIG. 6 depicts a flow chart of operations performed by the Interaction function, in an embodiment. In step 602, the Interaction function checks the patient's condition and possible drug interactions based on the patient's data. In step 604, the Interaction function returns the results, results2, of step 602. If the results of the interaction check indicate an error, then the IOT device programs sends a 'notice' message to the last person involved in the process, i.e., a person in the provider's office 102 and runs the Script function, in attempt to obtain an altered prescription that avoids the interaction.

Figure 7:
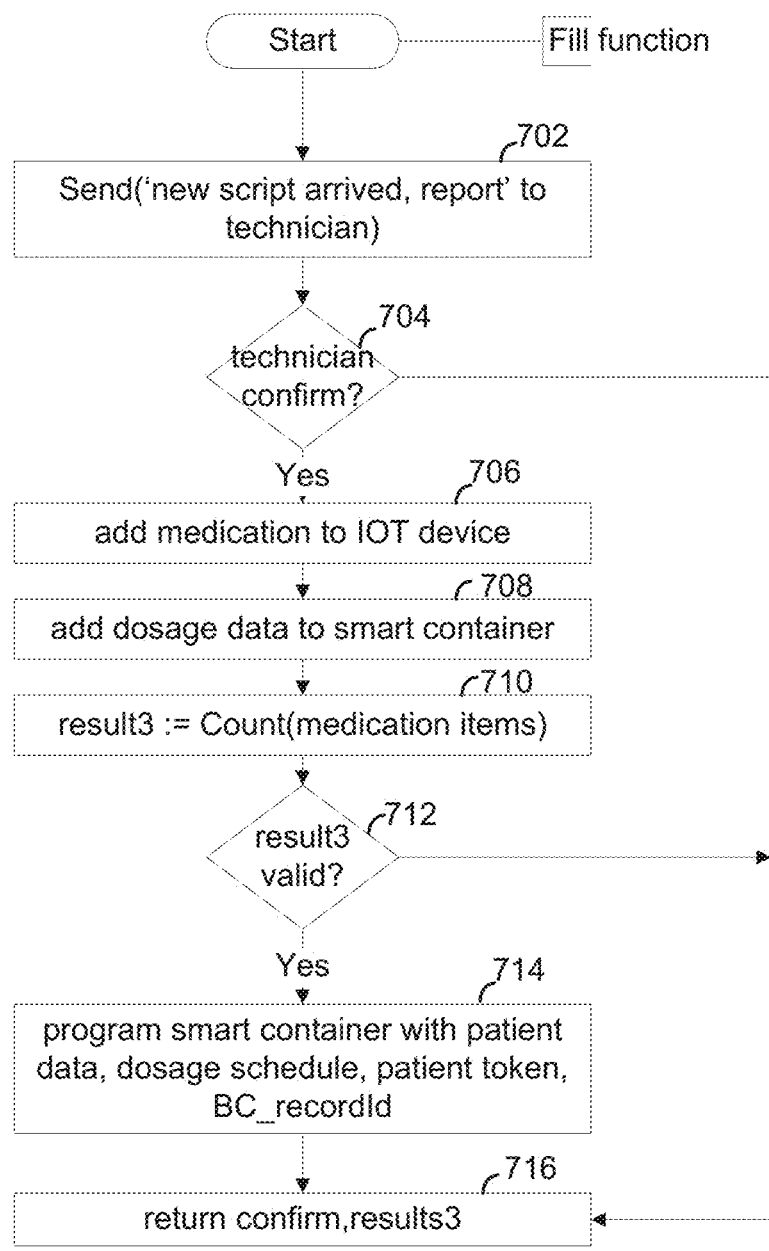
FIG. 7 depicts a flow chart of operations performed by the Fill function, according to one embodiment described herein.

FIG. 7 depicts a flow chart of operations performed by the Fill function, in an embodiment. In step 702, the Fill function sends a 'new script arrived, report' message to the pharmacy technician, where the report is the pharmacy report prepared in step 602 of FIG. 6. In step 704, the pharmacy technician checks the received report. If the pharmacy technician does not confirm the report as determined in step 704, then the Fill function returns with an error to inform the IOT device program. If the pharmacy technician does confirm the report as determined in step 706, then the patient's medication is added to the IOT device 114. In step 708, pharmacy technician adds dosage data to the smart and secure container 112. In step 710, the pill counting and sorting mechanism 206 of the IOT device 114 counts the medication items entering into the smart and secure container 112. This assures that the medication in the correct amount and in the proper form (size, color, shape and other markings) is added to the smart container. If, as determined in step 712, the result, results3, of the step 710 is invalid, then the Fill function returns with the results3 in the return value to inform the IOT device program 402 of the error. If the count is valid, then in step 714, the pharmacy technician programs the smart container and secure 112 with encrypted versions of the patient data, the patient's dosage schedule, the patient token and the record id of the block chain record, thereby ensuring that information stored in the smart container is secure. In step 716, the Fill function returns with its return values.

Figure 8:
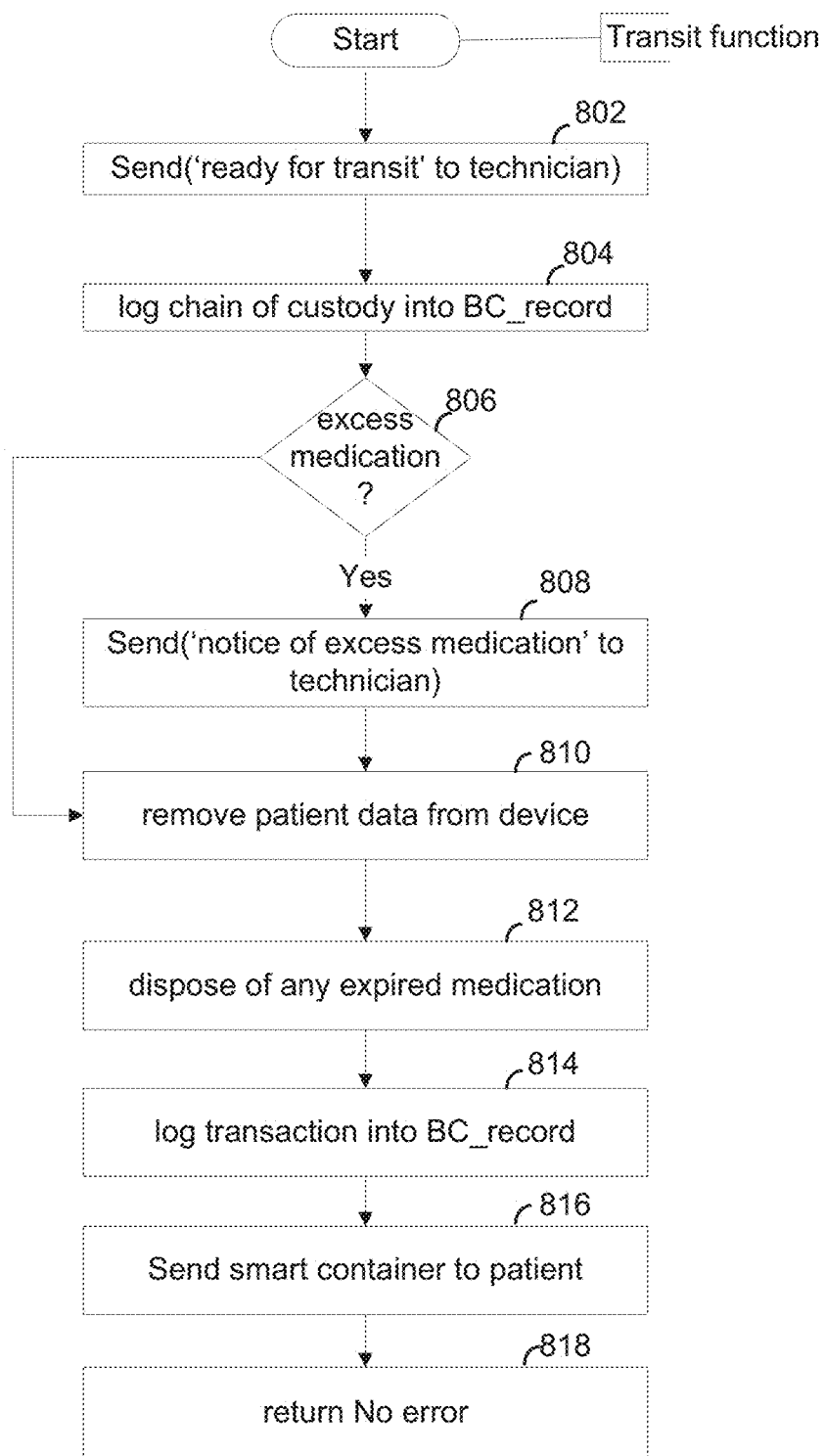
FIG. 8 depicts a flow chart of operations performed by the Transit function, according to one embodiment described herein.

FIG. 8 depicts a flow chart of operations performed by the Transit function, in an embodiment. In step 802, the Transit function sends a 'ready for transit' message to the pharmacy technician. In step 804, the Transit function logs the chain of custody into the block chain record. If step 806, the Transit function determines whether there is any excess medication. If so, then in step 808, the Transit function sends a 'notice of excess medication' message to the pharmacy technician. If not, then in step 810, the Transit function removes the patient data from the pharmacy IOT device 114 and in step 812 disposes of any expired medication. In step 812, the Transit function logs the transaction into the block chain record. In step 814, the Transit function has the smart and secure container 112 transported to the patient's site 106 and in step 816, returns with a 'No Error' return value.

Figure 9:
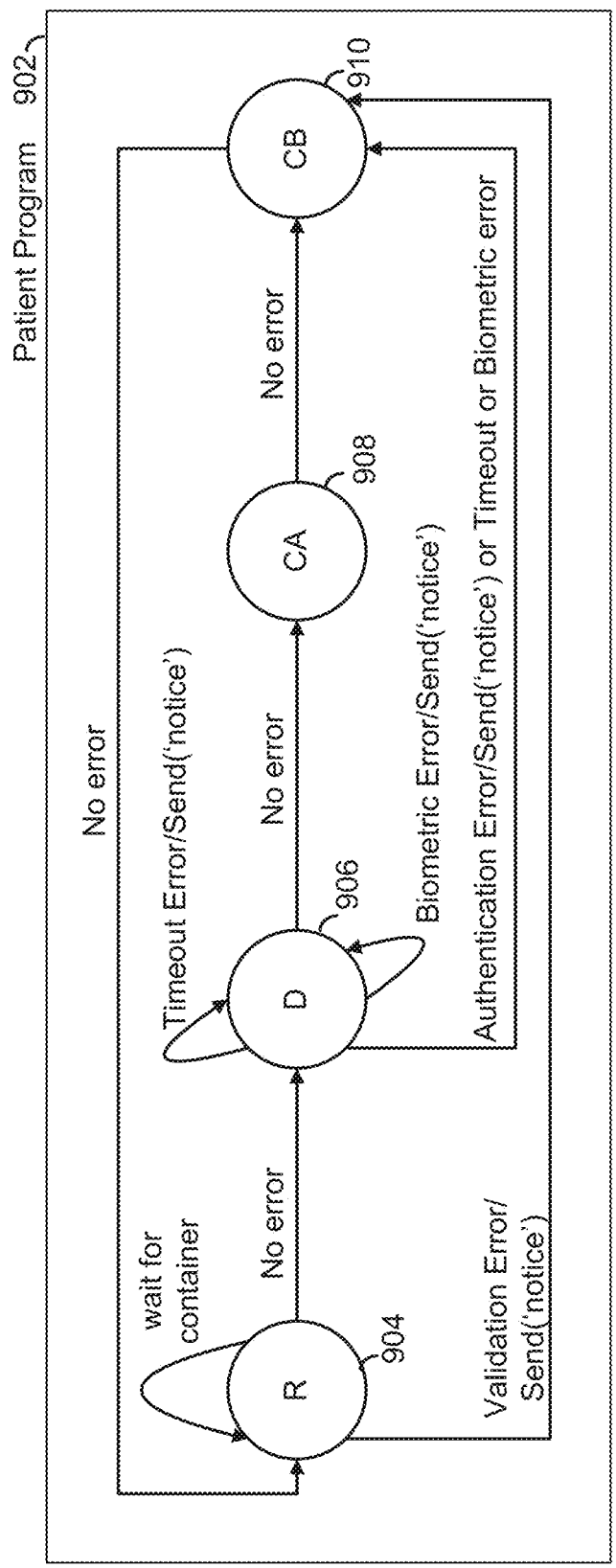
FIG. 9 depicts a flow chart of operations performed by the patient IOT device, according to one embodiment described herein.

FIG. 9 depicts a program run by the patient IOT device, in an embodiment. In the embodiment depicted, the program 902 has four states R 904, D 906, CA 908, and CB 910. In state R 904, the Replenishment function runs; in state D 906, the Dispense function runs; in state CA 908, the CompletionA function runs; and in state CB 910, the CompletionB function runs. Each of these functions is described in more detail below. In state R 904, the Replenishment function waits for a new smart container to arrive and if the function runs without error, then the program 902 runs the Dispense function next. If the Replenishment function encounters a validation error, then the program 902 sends a 'notice' message to the last person involved in the process (i.e., the pharmacy technician), and runs the CompletionB function next. If the Dispense function runs without error, then the program 902 runs the CompletionA function next. If the Dispense function encounters an authentication error, then the program 902 sends a 'notice' message to the last person involved in the process (i.e., the pharmacy technician) and runs the CompletionB function next. If the Dispense function encounters a Biometric error or a Timeout error, then the program 902 sends a 'notice' message to the pharmacy technician and runs the Dispense function next, attempting to see if the error can be avoided. If a Biometric error or Timeout error persists over a number of reruns of the Dispense function, program 902 may decide to run the Completion B function. If the CompletionA function runs without error then the program 902 runs the CompletionB function next. If the CompletionB function runs without error then the program 902 returns back to the Replenishment function, which waits for the next smart container to be attached. Thus, if no errors are encountered, the program 902 runs the Replenishment, Dispense, CompletionA and CompletionB functions sequentially. Besides the error conditions mentioned above, other error conditions can be accommodated by the existing functions or added functions.

Figure 10:
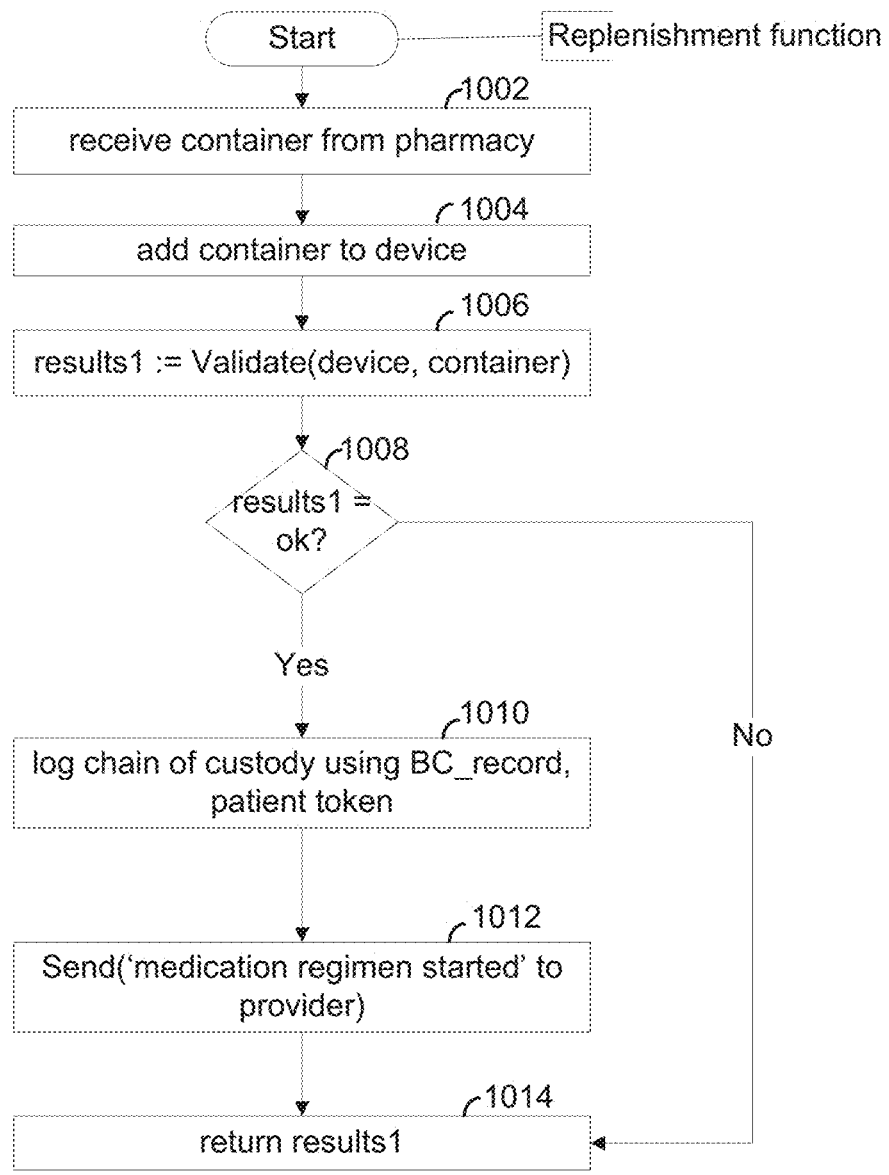
FIG. 10 depicts a flow chart of operations performed by the Replenishment function, according to one embodiment described herein.

FIG. 10 depicts a flow chart of operations performed by the Replenishment function, in an embodiment. In step 1002, the function has received a smart and secure container 118 from the pharmacy 104. In step 1004, the function connects the received smart and secure container 118 to the patient IOT device 122 via the USB port 252. In step 1006, the function validates the smart and secure container 118 against the patient IOT device 122 to determine if the smart and secure container 118 having the medication for the patient is connected to the correct IOT device 122 at the site of that patient 106. The validation is based on a public/private key combination stored in the smart container. If, as determined in step 1008, a validation error occurs, then the function executes step 1014 returning with a value for results1 indicating the error. If, as determined in step 1008, there is no validation error, then the function logs the chain of custody using the block chain record and the patient token. In step 1010, the function sends a 'medication regimen started' message to the provider's office 102, and then in step 1014, returns.

Figure 11:
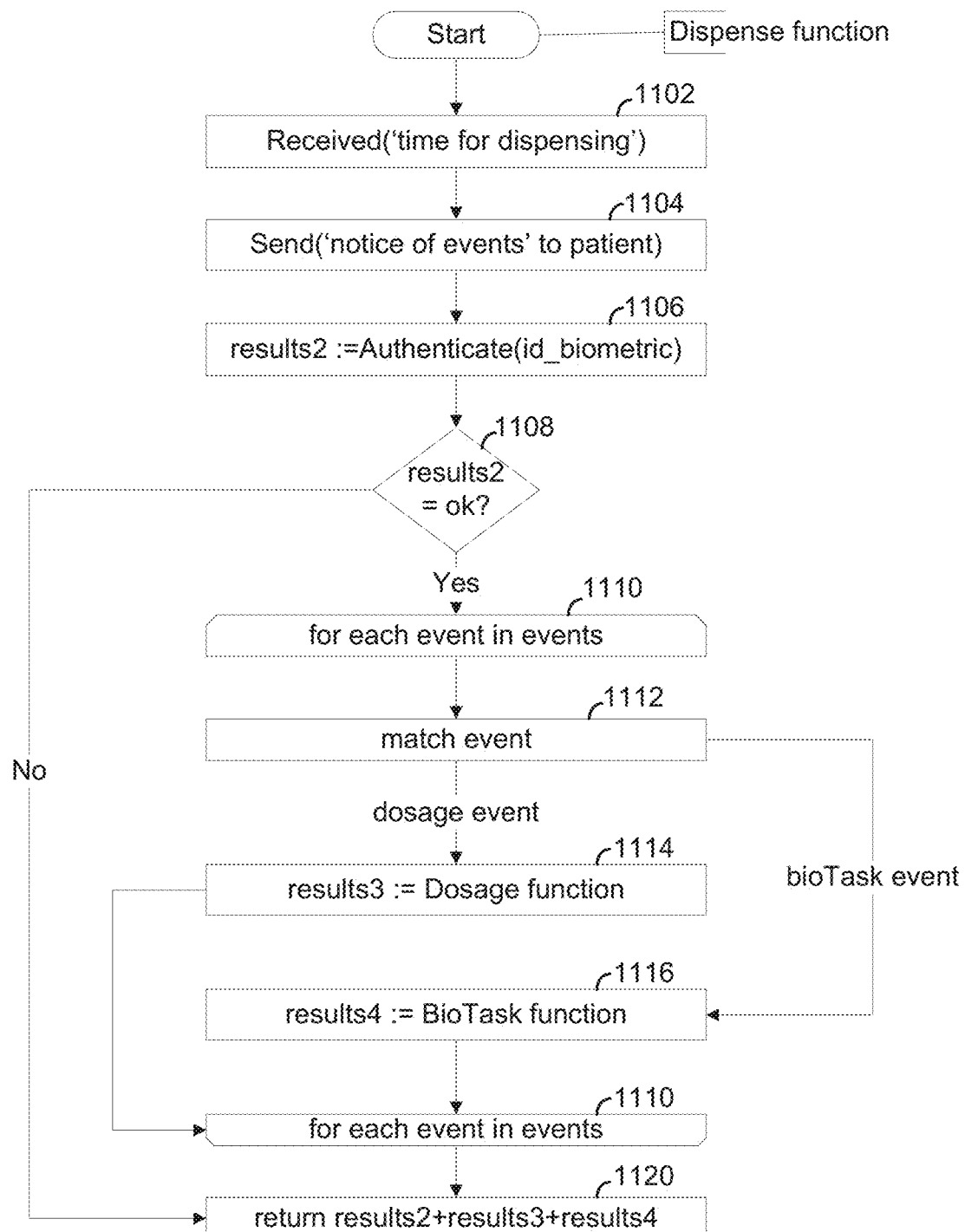
FIG. 11 depicts a flow chart of operations performed by the Dispense function, according to one embodiment described herein.

FIG. 11 depicts a flow chart of operations performed by the Dispense function, in an embodiment. In step 1102, the function awaits a time of day at which medication is to be dispensed. In step 1104, the function sends a 'notice of events' message to the patient indicating a number of bioTasks (biomedical measurements) and/or dosage events (time of day and particular medication) that the patient must successfully complete in carrying out the prescription. Notification can include an audio signal or an electronic alert such as a text message, email, or phone call with a message. In step 1106, the Dispense function authenticates the identity of the patient via a biometric id such as a fingerprint, using the authentication device 234 attached to the IOT device 122 at the patient's site 106. If, as determined in step 1108, the results of the authentication fail, then the Dispense function executes step 1120 returning with 'results2' indicating the authentication failure. If, as determined in step 1108, the authentication succeeds, then in step 1110 the function starts an iterator over the various events (tasks) required of the patient to receive the medication. In step 1112, match event determines whether the event is dosage event or a bioTask event. If the event is a dosage event, then the function invokes the Dosage function in step 1114 to provide the medication. If the event is a bioTask event, then the function invokes in step 1116 the BioTask function, which captures one or more bio-measurements performed by the patient. In step 1120, the function returns with the results of the Dosage and BioTask functions.

Figure 12:
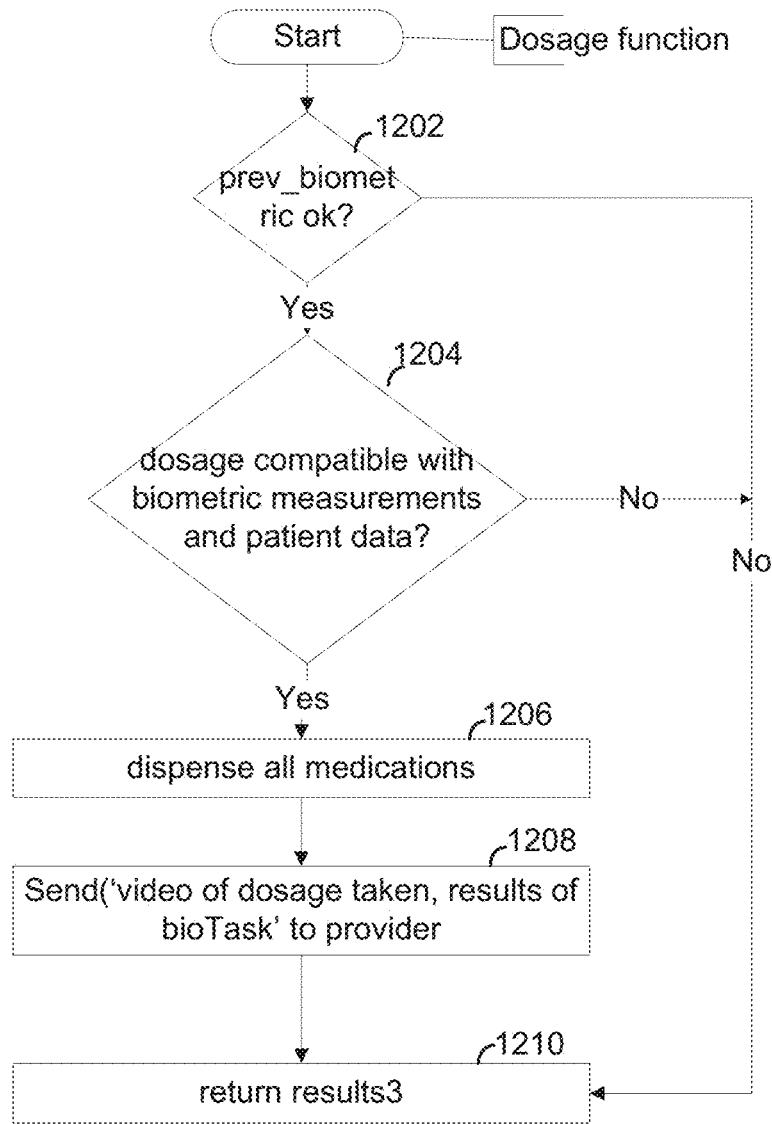
FIG. 12 depicts a flow chart of operations performed by the Dosage function, according to one embodiment described herein.

FIG. 12 depicts a flow chart of operations performed by the Dosage function, in an embodiment. In step 1202, the function determines whether any previous biometric measurement or measurements based on the variable prey biometric, returned an error. If so, then medication is not dispensed. If result of a previous BioTask function is acceptable, then in step 1204, the function determines whether the dosage is compatible with the biometric measurements and the patient data, which is stored in the memory of the smart container. If the dosage is compatible, then the Dosage function dispenses the medications in step 1206 in amounts in accordance with the results of the biometric measurements combined with the patient's data. In step 1208 sends a 'video of dosage taken, results of bioTask' message to the provider's office 102 over link C 128, where the message includes the actual video, using the video camera 256 at the patient's site 122, of the patent taking the medication and the results of the BioTask or BioTasks that were required prior to and as a condition of administering the medication or were required after taking the medication. Sending this information to the provider's office helps determine whether the mediation had the desired effect. In step 1210, the function returns with 'results3'. 'Results3' indicate no error if the medication was dispensed or the biometric tests and/or the results of the compatibility of the dosage with the combined biometric measurements and the patent data, thus indicating the reason that the medication was not dispensed. As described in reference to FIG. 9, the patient program then decides whether or not to repeat the Dispense function.

Figure 13:
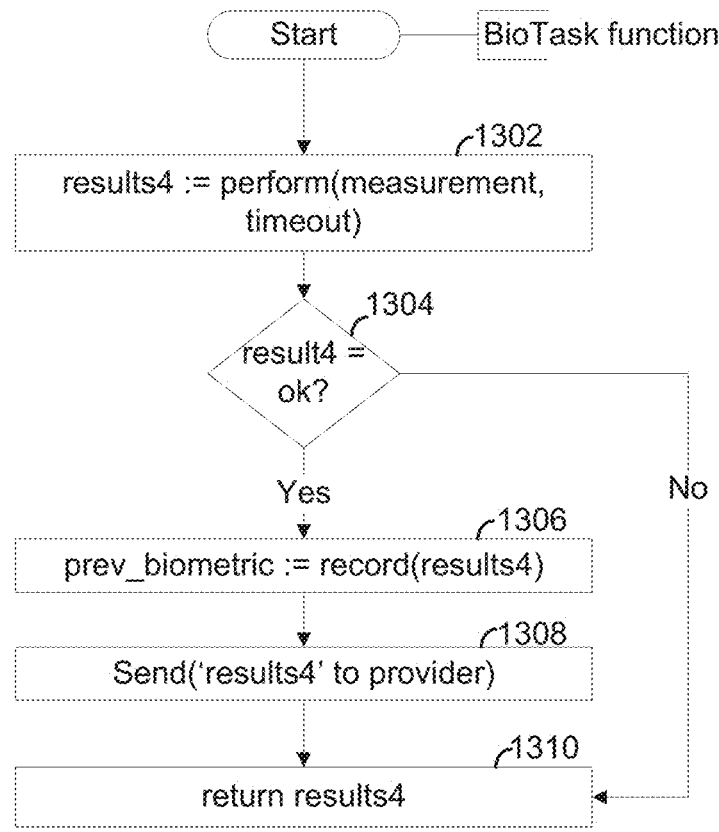
FIG. 13 depicts a flow chart of operations performed by the BioTask function, according to one embodiment described herein.

FIG. 13 depicts a flow chart of operations performed by the BioTask function, in an embodiment. In step 1302, the patient performs a requested biometric task, such as measuring blood pressure, blood oxygen level, heart rate, glucose levels and temperature, using biometric devices 254. If, as determined in step 1304, the results are acceptable (i.e., within acceptable limits), then the function records the results of the biometric in a variable, prev_biometric, and in step 1306, sends a results message, 'results4' of the biometric measurement to the provider's office 102 and returns in step 1310. If, as determined in step 1304, the results of the measurement are not acceptable, either because the measured values are not valid or out of range or because a time period in which the measurement was to be performed had elapsed (i.e., a timeout), then the function returns in step 1310 with the results. The patient program 902 running on the patient IOT device then sends a 'notice' message to the last person involved in the process, the pharmacy technician, and then runs the BioTask function again. After a certain number of attempts at re-running the BioTask function, the patient program 902 may decide to end the process by running the CompletionB task and sending a 'notice' message to the medical provider.

Figure 14:
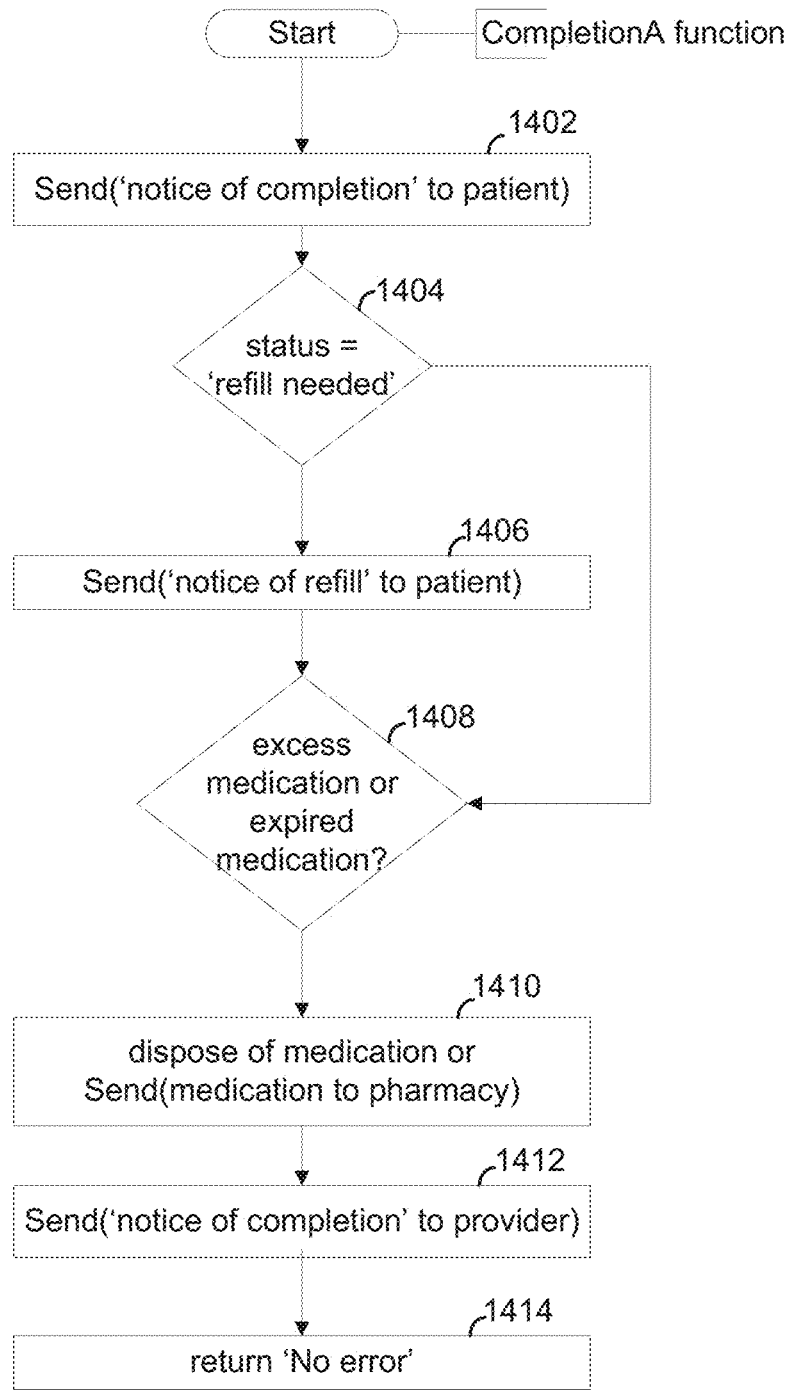
FIG. 14 depicts a flow chart of operations performed by the CompletionA function, according to one embodiment described herein.

FIG. 14 depicts a flow chart of operations performed by the CompletionA function, in an embodiment. In step 1402, the function sends a 'notice of completion' message to the patient. In step 1404, the function determines whether or not a refill of medication is needed based on an inventory of medications in the smart and secure container 118. If so, then in step 1406 the function sends a 'notice of refill' to the patient. If not, then the function determines in step 1408 whether there is any excess medication or expired medication. If so, then in step 1410, the function causes the disposal of the medication using the neutralization container 310 or causes the medication in the smart container to be sent back to the pharmacy. In step 1412, the function sends a 'notice of completion' to the provider's office 102 and returns in step 1414.

Figure 15:
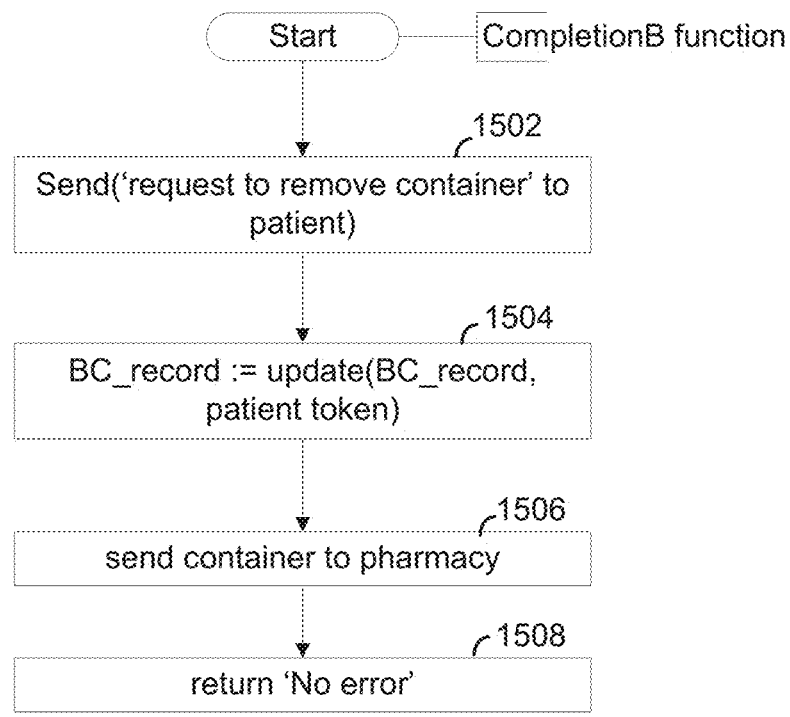
FIG. 15 depicts a flow chart of operations performed by the CompletionB function, according to one embodiment described herein.

FIG. 15 depicts a flow chart of operations performed by the CompletionB function, in an embodiment. In step 1502, the function sends a 'request to remove container' message to the patient, which causes removal of the smart and secure container 118 from the IOT device 122 at the patient's site 106. In step 1504, the function updates the block chain record using the patient token to record the removal of the smart and secure container 118. In step 1506, the function causes the smart and secure container 118 to be returned to the pharmacy 104 and in step 1508, returns with 'No error'.

Figure 16:
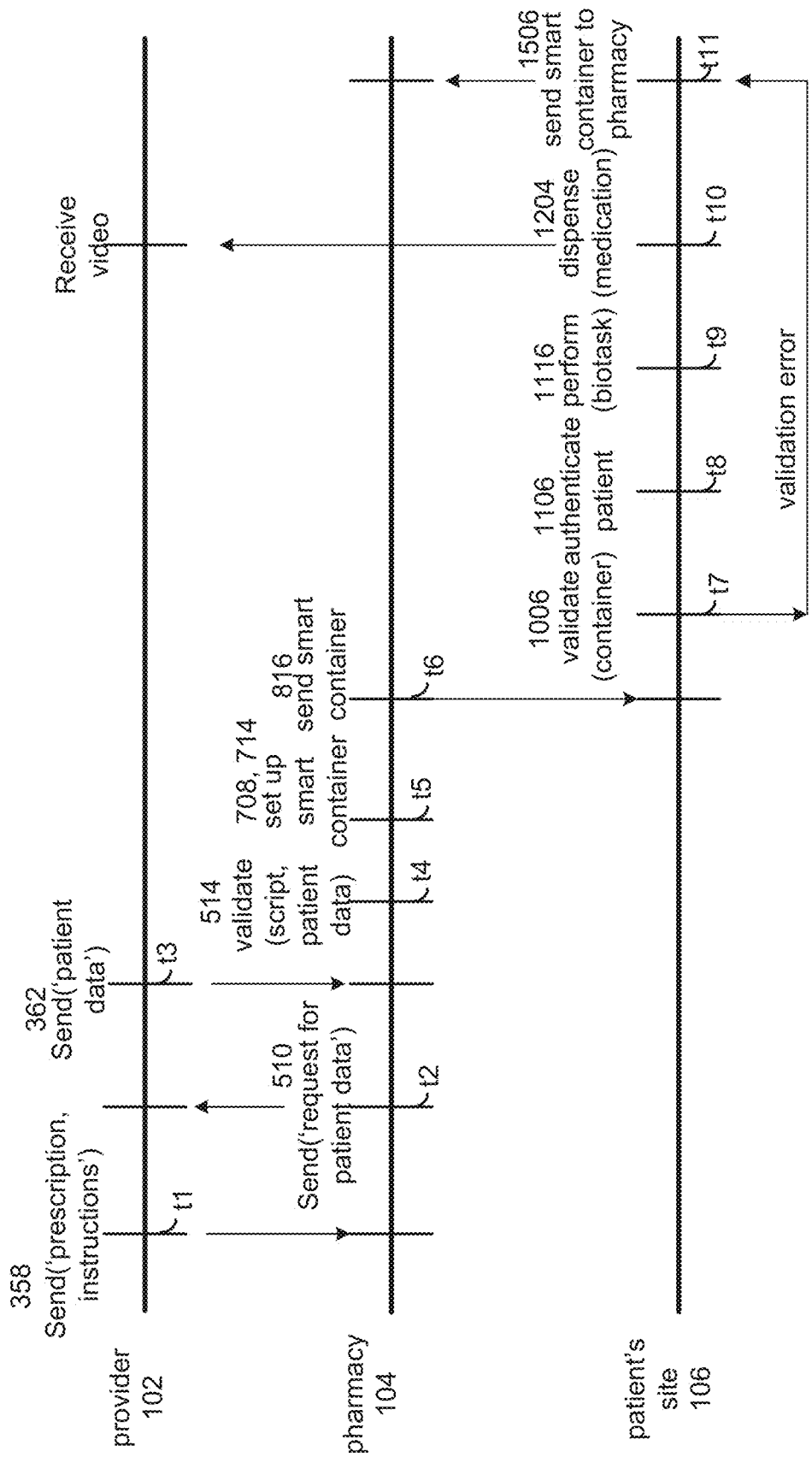
FIG. 16 depicts a time line of various operations, according to one embodiment described herein.

FIG. 16 depicts a time line, in summary fashion, of various events, in an embodiment. At time t1, the provider sends the prescription and instructions to the pharmacy 104. At time t2, the pharmacy 104 requests the patient data and at time t3 receives the requested patient data from the provider 102. At step t4, the pharmacy 104 validates the prescription against the received patient data. At time t5, the pharmacy 104 sets up the smart and secure container 112 and at time t6 sends the smart and secure container 112 to the patient's site 106. At time t7, the patient's site 106 validates the smart and secure container 118 at the patient's site 106. At time t8, the patient's identity is authenticated. A time t9, the patient performs any bioTasks that are conditions for receiving the medication. At time t10, the patient's medication is dispensed via the smart and secure container 118 and a video of the patent taking the medication is sent back to the provider 102. At time t11, the smart and secure container 118 is returned to the pharmacy 104.

The result of these processes is that prescriptions from a medical provider can be securely and accurately delivered to a pharmacy, that the pharmacy perform a test for medication interactions based on the patient's data, and can securely fill the prescription with the correct dosage, correct amount and correct form of the medication, that the medication can be securely transported to the patient's site, that the identity and physical condition of the patient can be checked before medication is dispensed according to a prescribed time schedule and that any unused medication can be disposed of or returned to the pharmacy.

Because a complete chain of custody from the time that the medical provider prescribed the medication to the filling of the prescription at the pharmacy to the taking of the medication by the patient is recorded by the block chain records, the chain of custody can be used for further treatment, and/or related medical analysis (i.e., clinical trials, insurance payments, drug usage analysis, patient consumption patterns, pharmacy inventory reconciliation and doctor prescription analysis.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the present disclosure, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the described aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A computer-readable storage medium having computer-readable program code embodied therewith, the computer-readable code executable by one or more computer processors to perform an operation comprising:
   receiving, from a medical provider, a prescription associated with an identifier of a patient;
   in response to receiving the prescription, requesting and obtaining, from the medical provider, patient data including medical history of the patient;
   determining that the prescription is compatible with the patient data;
   adding medication according to the prescription to a secure container, wherein:
      the secure container includes a memory,
      the secure container includes disposal bins which store disposed medication, and
      the secure container is configured to dispose of medication by adding a neutralizing agent to the medication and then causing the neutralized medication to be deposited into the disposal bins; and
   updating the memory of the secure container with the patient identifier and dosage information, including a dosage schedule according to the received prescription.

2. The computer-readable storage medium of claim 1, the operation further comprising:
   receiving encrypted electronic data containing the prescription over the Internet; and
   decrypting the encrypted electronic data to generate the prescription in plain text.

3. The computer program product computer-readable storage medium of claim 1,
   wherein the patient data includes other medication prescribed for the patient; and
   wherein determining that the prescription is compatible with the patient data comprises determining that the medication prescribed does not adversely interact with the other patient medication.

4. The computer-readable storage medium of claim 1, wherein adding medication to the secure container comprises:
   receiving an indication that the secure container is connected to a medication counting and sorting mechanism; and
   causing the medication counting and sorting mechanism to fill one or more bins of the secure container with the medication.

5. The computer-readable storage medium of claim 1, wherein causing the medication counting and sorting mechanism to fill the one or more bins of the secure container with the medication includes counting the medication as the one or more bins are filled.

6. The computer-readable storage medium of claim 1, wherein:
   the secure container is transported to a site at which the patient is present; and
   the patient receives the medication after the identity of the secure container is verified at the patient site based on the patient identifier in the memory of the secure container and identity of the patient is authenticated based on a biometric scan.

7. The computer-readable storage medium of claim 6, wherein a video recording of the patient at the patient site receiving and taking the medication is sent to the medical provider.

8. The computer-readable storage medium of claim 1, the operation further comprising:
   creating a block chain record for inclusion in a distributed ledger;
   updating the block chain record with a pharmacy token to identify the pharmacy that received the prescription;
   updating the block chain record with a patient token based on the identifier of the patient to identify the patient for whom the prescription was received; and
   updating the block chain record with a transaction identifying the adding of medication into the secure container.

9. A computer-readable storage medium having computer-readable program code embodied therewith, the computer-readable code executable by one or more computer processors to perform an operation comprising:
- receiving, from a medical provider, a prescription associated with an identifier of a patient;
- in response to receiving the prescription, requesting and obtaining, from the medical provider, patient data including medical history of the patient;
- determining that the prescription is compatible with the patient data;
- adding medication according to the prescription to a secure container, wherein the secure container includes a memory;
- updating the memory of the secure container with the patient identifier and dosage information, including a dosage schedule according to the received prescription;
- creating a block chain record for inclusion in a distributed ledger;
- updating the block chain record with a pharmacy token to identify the pharmacy that received the prescription;
- updating the block chain record with a patient token based on the identifier of the patient to identify the patient for whom the prescription was received; and
- updating the block chain record with a transaction identifying the adding of medication into the secure container.

10. The computer-readable storage medium of claim 9, the operation further comprising:
- receiving encrypted electronic data containing the prescription over the Internet; and
- decrypting the encrypted electronic data to generate the prescription in plain text.

11. The computer-readable storage medium of claim 9,
- wherein the patient data includes other medication prescribed for the patient; and
- wherein determining that the prescription is compatible with the patient data comprises determining that the medication prescribed does not adversely interact with the other patient medication.

12. The computer-readable storage medium of claim 9, wherein adding medication to the secure container comprises:
- receiving an indication that the secure container is connected to a medication counting and sorting mechanism; and
- causing the medication counting and sorting mechanism to fill one or more bins of the secure container with the medication.

13. The computer-readable storage medium of claim 9, wherein causing the medication counting and sorting mechanism to fill the one or more bins of the secure container with the medication includes counting the medication as the one or more bins are filled.

14. The computer-readable storage medium of claim 9, wherein the secure container includes disposal bins which store disposed medication.

15. The computer-readable storage medium of claim 14, wherein the secure container is configured to dispose of medication by adding a neutralizing agent to the medication and then causing the neutralized medication to be deposited into the disposal bins.

16. The computer-readable storage medium of claim 9, wherein:
- the secure container is transported to a site at which the patient is present; and
- the patient receives the medication after the identity of the secure container is verified at the patient site based on the patient identifier in the memory of the secure container and identity of the patient is authenticated based on a biometric scan.

17. The computer-readable storage medium of claim 16, wherein a video recording of the patient at the patient site receiving and taking the medication is sent to the medical provider.

* * * * *